Figure 1A:
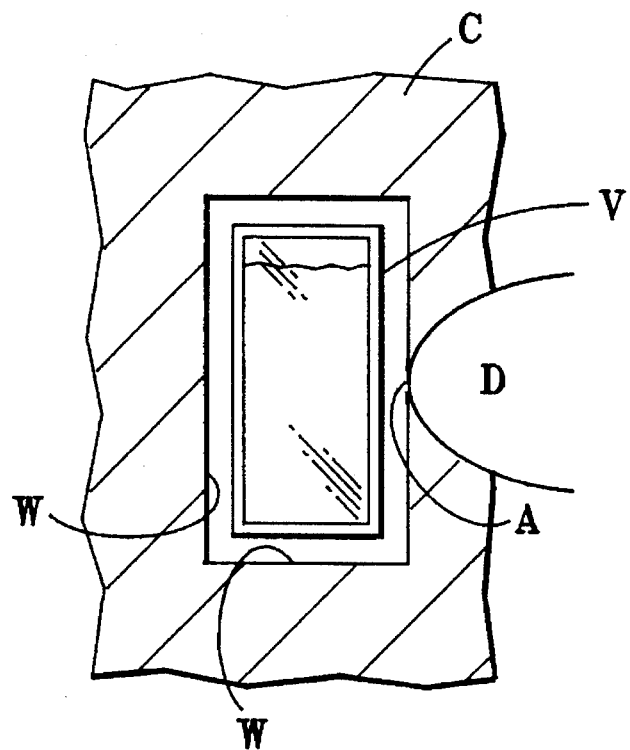

United States Patent [19]

Springsteen et al.

[11] Patent Number: 5,488,473
[45] Date of Patent: Jan. 30, 1996

[54] METHOD OF AND APPARATUS FOR INCREASING MEASUREMENT SENSITIVITY OF FLUORESCENCE AND LUMINESCENCE

[75] Inventors: Arthur W. Springsteen, New London, N.H.; Jeffrey L. Taylor, Mt. Airy, Md.

[73] Assignee: Labsphere, Inc., N. Sutton, N.H.

[21] Appl. No.: 204,830

[22] Filed: Mar. 1, 1994

[51] Int. Cl.⁶ ............................ G01N 21/64; G01N 21/76
[52] U.S. Cl. .................. 356/317; 250/228; 250/458.1; 356/417; 356/236
[58] Field of Search ............................ 356/417, 317, 356/318, 236; 250/458.1, 459.1, 361 C, 228

[56] References Cited

U.S. PATENT DOCUMENTS

| | | | |
|---|---|---|---|
| 3,764,214 | 10/1973 | Heiss | 250/458.1 X |
| 3,826,574 | 7/1974 | Brown, Jr. | 356/236 X |
| 4,488,814 | 12/1984 | Johnson | 356/417 X |
| 5,082,628 | 1/1992 | Andreotti et al. | 250/361 C X |
| 5,317,378 | 5/1994 | Mould et al. | 356/236 X |

*Primary Examiner*—Vincent P. McGraw
*Attorney, Agent, or Firm*—Rines and Rines

[57] ABSTRACT

A technique and apparatus for increased sensitivity fluorescence and luminescence emission measurements in which the emission volume is enclosed in a closely fitting cavity having highly reflecting diffuse material inner walls, and with a detector viewing as much of the radiant cavity walls as possible.

4 Claims, 1 Drawing Sheet

METHOD OF AND APPARATUS FOR INCREASING MEASUREMENT SENSITIVITY OF FLUORESCENCE AND LUMINESCENCE

The present invention relates to techniques and apparatus for measuring the fluorescence and luminescence of light, being more particularly concerned with the measurement and analyses of the emitted light and of the spectral content of fluorescent and/or luminiscent emissions.

BACKGROUND

The phenomena of light fluorescence and luminescence, stimulated in surfaces of various types by the impingement of incident light or other radiation, are generally characterized by such fluorescent or luminescent light radiation or emission occuring over or from a relatively large volume, and in an omnidirectional fashion. Such omnidirectional emission from a large volume results in low radiance, making it difficult to capture enough of the emitted energy in optical detector instruments to perform desired analyses, including high sensitivity measurements of the amount of emitted light and of its spectral content.

Though attempts have been made to solve this problem through the use of conventional optical techniques, including optical systems with specular surfaces (mirrors) and appropriate focusing lenses and the like and dedicated luminometers, such have not been totally successful and have had serious limitations in sensitivity.

Underlying the present invention, on the other hand, is a discovery of a rather radical departure from such optical measurement techniques residing in enclosing the fluorescing or luminescing volume within a closely fitting cavity formed of highly reflecting diffuse material walls, remarkably to improve the measurement sensitivity of the detector optical system, viewing as much of the cavity radiant wall as possible.

OBJECTS OF INVENTION

A primary object of the present invention, accordingly, is to provide a new and improved method of and apparatus for fluorescence and/or luminescence measurements that significantly improve the measurement sensitivity over prior optical detecting systems and is not subject to the limitations thereof.

Other and further objects will be explained hereinafter and are more particularly pointed out in the appended claims,

SUMMARY

From one of its view points, the invention, in summary, embraces a method of increasing the sensitivity of measurement of fluorescing and/or luminescing light emitted from a volume, that comprises, enclosing the emission volume in a closely fitting cavity enclosure; providing the inner walls of the cavity enclosure with a highly reflecting diffuse material to enable all the light emitted from the emission volume inside the cavity to contribute to the radiance of the cavity inner walls, and the multiple reflections therefrom to increase the wall radiance; and positioning a detector to maximize its view of the radiant walls.

Preferred and best mode techniques and apparatus are hereinafter set forth.

DRAWINGS

The invention will now be described in connection with the accompanying drawings, FIGS. 1A and 1B of which are longitudinal cross-section and top elevational views, respectively, of a preferred apparatus operating in accordance with the method of the invention.

PREFERRED EMBODIMENTS

Figure 1B:
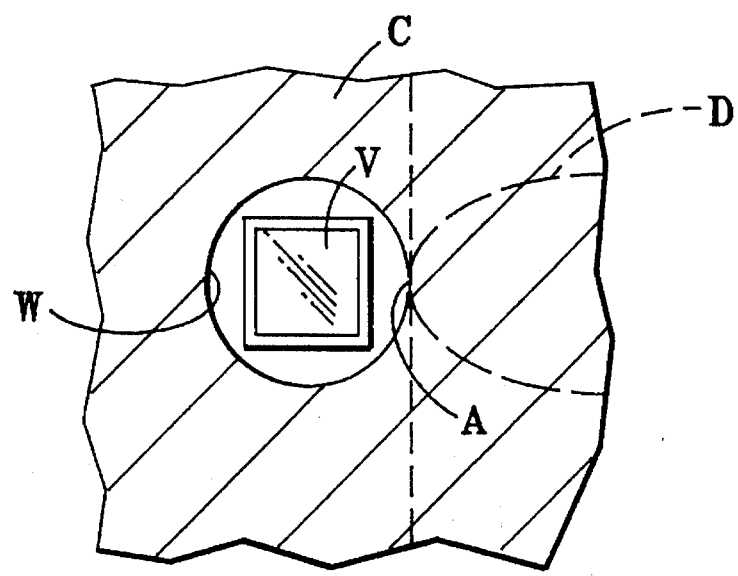

The discovery underlying the invention, as before explained, resides in the synergistic effect resulting from enclosing a volume V, such as a transparent cuvette or cell in FIGS. 1A and 1B, containing bioluminescent or chemiluminescent or similar material producing continually fluorescing and/or luminescing emissions, within a closely fitting cavity enclosure or sleeve C the inner walls W of which are coated with or made of a highly reflecting diffuse material, as of the sintered polytetrafluoroethylene and other material types described, for example, in prior U.S. Pat. No. 4,912,720.

In this manner, all of the fluorescing or luminescing surface light emitted within or inside the cavity C contributes continually to the radiance of the adjacent cavity inner walls W. Due to the multiple reflections from the highly reflecting diffuse inner cavity walls, furthermore, the radiance of the walls is increased even further.

With the detector D internally positioned to maximize the view of as much of the radiant wall surface as possible (normally limited by the optical system of the detector), it has been found that very significant increases in the measurement sensitivity of fluorescence-and luminescence-emitted light, spectral content and other characteristics can be achieved.

Among useful applications are the measurement of bioluminescence or chemiluminescence of self-illuminating or chemical or radiation-initiating luminescing liquids or the like. Such, in accordance with the invention, may be contained in transparent cell volumes V which are lowered into or otherwise encased, enclosed or surrounded by the preferably rather closely fitting outer cavity enclosure or sleeve C, the adjacent inner walls W of which are of the before-described highly reflecting diffuse material, such that substantially all the luminescent light from the cell is emitted into the adjacent cavity walls to contribute to the radiance of the walls, and with the multiple reflections therefrom increasing the wall radiance.

The cavity enclosures may be of cylindrical (FIGS. 1A and 1B), spherical, cubical or other configurations depending upon the shape of the luminescing or fluorescing volume V. The photodetector D, luminometer or other detecting-viewing system views the cavity inner walls as in or through an aperture A therein, located centrally, as shown, to maximize its view of the cavity inner wall surfaces. Fluorescing volumes may be of the order of a cubic centimeter, with slightly larger cavity sleeves, and with a useful range of from, say, one tenth to ten times such volume for these types of applications.

As an example, with fluorescing fluid cells fitted within a cylindrical cavity (FIGS. 1A and 1B) having the before-described diffuse highly reflecting inner walls and about 1½ inches in diameter and about 3 inches long, sensitivities in measurement below 1 femtogram have been obtained, far more sensitive than measurements obtained with dedicated luminometers.

The system may be used as an accessory with conventional measurement apparatus such as, for example, the Perkin-Elmer LS50B type, involving a built in integrating sphere to maximize sensitivity and an injector port (such as from the top in FIG. 1B), to allow the addition of analyte in situ.

Further modifications will occur to those skilled in this art, and such are considered to fall within the spirit and scope of the invention as defined in the appended claims.

What is claimed is:

1. A method of increasing the sensitivity of measurement of fluorescing and/or luminescing light emitted from a volume, that comprises, enclosing the emission volume in a relatively closely fitting cavity enclosure; providing all of the inner walls of the cavity enclosing the volume with a highly reflecting diffuse material to enable all the light emitted from the emission volume inside the cavity to contribute to the radiance of the cavity inner walls, and the multiple reflections therefrom to increase the wall radiance; and positioning a detector to maximize its view of the radiant walls.

2. A method as claimed in claim 1 and in which the detector means is positioned for exposure through an aperture located substantially centrally of a wall of the cavity to enable said maximum view of the radiant walls.

3. For measuring the fluorescence and/or luminescence emitted from a volume, a cavity of dimensions slightly larger than the volume adapted to enclose such fluorescing and/or luminescing volume and enabling multiple reflections from the inner walls of the cavity, all of the inner cavity walls enclosing the volume being of highly reflecting diffuse material to enable the the fluorescing or luminescing light emitted inside the cavity to contribute to the radiance of the inner walls, and the multiple reflections therefrom to increase the wall radiance; and detector means positioned to maximize its view within the cavity of the radiant walls.

4. Apparatus as claimed in claim 3 and in which the detector means is exposed through an aperture located substantially centrally of a wall of the cavity to enable said maximum view of the radiant walls.

* * * * *